(12) United States Patent
Gogolak

(10) Patent No.: US 7,461,006 B2
(45) Date of Patent: Dec. 2, 2008

(54) METHOD AND SYSTEM FOR THE ANALYSIS AND ASSOCIATION OF PATIENT-SPECIFIC AND POPULATION-BASED GENOMIC DATA WITH DRUG SAFETY ADVERSE EVENT DATA

(76) Inventor: Victor Gogolak, 934 Douglass Dr., McLean, VA (US) 22101

( * ) Notice: Subject to any disclaimer, the term of this patent is extended or adjusted under 35 U.S.C. 154(b) by 1009 days.

(21) Appl. No.: 10/229,119

(22) Filed: Aug. 28, 2002

(65) Prior Publication Data

US 2003/0046110 A1 Mar. 6, 2003

Related U.S. Application Data

(60) Provisional application No. 60/315,525, filed on Aug. 29, 2001.

(51) Int. Cl.
*G06Q 10/00* (2006.01)
(52) U.S. Cl. ............................ 705/2; 705/3; 707/101; 707/104.1; 704/233; 600/300; 435/5
(58) Field of Classification Search ............... 600/300; 705/2, 3; 707/101, 104.1; 715/101, 500; 435/5; 704/233
See application file for complete search history.

(56) References Cited

U.S. PATENT DOCUMENTS

| | | | |
|---|---|---|---|
| 5,833,599 A * | 11/1998 | Schrier et al. ............... 600/300 |
| 5,991,729 A * | 11/1999 | Barry et al. ................... 705/3 |
| 6,000,828 A * | 12/1999 | Leet ............................... 705/2 |
| 6,014,631 A * | 1/2000 | Teagarden et al. ............. 705/3 |
| 6,054,268 A * | 4/2000 | Perlin ............................ 506/4 |
| 6,055,538 A * | 4/2000 | Kessenich et al. ........... 707/101 |
| 6,209,004 B1 * | 3/2001 | Taylor ........................ 715/500 |
| 6,219,674 B1 * | 4/2001 | Classen .................... 707/104.1 |
| 6,317,719 B1 * | 11/2001 | Schrier et al. .................. 705/2 |
| 6,466,923 B1 * | 10/2002 | Young ......................... 706/13 |
| 6,542,902 B2 * | 4/2003 | Dulong et al. ........... 707/104.1 |
| 6,578,003 B1 * | 6/2003 | Camarda et al. .............. 705/3 |
| 6,876,966 B1 * | 4/2005 | Deng et al. ................. 704/233 |
| 6,950,755 B2 * | 9/2005 | Stahl ........................... 702/19 |
| 2003/0124514 A1 * | 7/2003 | Vingerhoets et al. .......... 435/5 |

\* cited by examiner

*Primary Examiner*—C Luke Gilligan
*Assistant Examiner*—Dilek B Cobanoglu
(74) *Attorney, Agent, or Firm*—Morrison & Foerster LLP

(57) ABSTRACT

A method for assessing and analyzing one or more drugs, adverse effects and associated risks, and patient characteristics resulting from the use of at least drug of interest is disclosed. The method comprises the steps of selecting one or more cases for analysis, said cases describing the behavior between at least one drug of interest and a patient genotype; profiling statistically derived values from multiple cases related to the safety of the at least one drug, wherein at least one filter is employed for deriving said values; at least one data mining engine; and an output device for displaying the analytic results from the data mining engine. A system for performing the method is likewise disclosed.

40 Claims, 3 Drawing Sheets

METHOD AND SYSTEM FOR THE ANALYSIS AND ASSOCIATION OF PATIENT-SPECIFIC AND POPULATION-BASED GENOMIC DATA WITH DRUG SAFETY ADVERSE EVENT DATA

RELATED APPLICATIONS

This application claims benefit of U.S. Provisional Application No. 60/315,525 filed Aug. 29, 2001. This application is related to each of the following applications: U.S. patent application Ser. No. 09/681,586 filed May 02, 2001; U.S. patent application Ser. No. 09/681,587 filed May 2, 2001; U.S. patent application Ser. No. 09/681,583 filed May 2, 2001; U.S. patent application Ser. No. 09/845,722 filed May 2, 2001, the disclosures of which are incorporated herein by reference in their entireties.

TECHNICAL FIELD

The present invention relates to a drug safety database. More particularly, the invention relates to a method and system for creating and utilizing a database that relates drugs, adverse events, patient characteristics, and in particular, genetic information.

BACKGROUND OF THE INVENTION

Publicly and privately developed pharmacological data is readily available from both reference data and source data. Statistical information has been collected for many years on adverse reactions to drugs, including information on prescriptions, nutraceuticals, and over-the-counter medications. With this information, databases have been created that provide both reporting and data analysis of adverse drug reactions. Typically, this data is provided in a format that is not amenable to searching, such as in ASCII format.

Additionally, these databases are often in different structures and language formats, decreasing the efficiency and impeding effective use. Further, the variations in terminology and software languages employed by these disparate databases complicates conventional queries, making the results unreliable.

Various methods and techniques have been developed to address the need to provide ready access to pharmacological data and adverse events. However, none of these partial solutions, such as the Freedom of Information data provided by the FDA (which relies on "flat files") or standard dictionaries such as the Medical Dictionary for Regulatory Activities (MedDRA™), have been integrated to allow consistent analysis and results.

Pharmacogenetics is the study of individual response to drugs as a function of genetic differences. These responses relate to how a drug functions in any given individual, how it is metabolized, its toxicity and dosage requirements. With the human genome project, pharmacogenetics has expanded into pharmacogenomics. Pharmacogenomics goes beyond pharmacogenetics, with the potential to find uses from drug discovery and development, target discovery and validation, and clinical trials; and to get that information into the doctor's office so that the right medicine is given to the right patient at the right time.

For pharmacogenomics to be effective, markers are needed that are indicative of the connection between drug response and genetic makeup. One such marker that is being diligently pursued is the single-nucleotide polymorphism (SNP). Databases are presently available that furnish a map of over a million SNPs. From this data, information has been collected regarding the allelic frequency of a SNP within an ethnically diverse population. There are also other databases which are more narrowly tailored and focus only on particular groups of SNPs such as those that code for proteins; provide a data set related to ADME (absorption, distribution, metabolism and excretion) genes and SNPs that are associated with how the body responds to drugs. Instead of single SNPs, some databases focus on SNPs that are found in haplotypes, which work together to cause a particular drug response.

Pharmacogenomics is being applied to pharmacodynamics, how a drug affects a disease. Additionally, pharmacogenomics is being applied to pharmacokinetics, or how the body processes a drug. While the pathway for drug intervention is usually well known, there are two important mechanisms to consider in pharmacokinetics—the pathway that metabolizes the drug itself, and other pathways that drugs and their metabolites may inadvertently and adversely affect. It is in these two areas that drug safety comes into play. In the first, there are distinctions among human genotypes in the ability to metabolize drugs. If a drug is not metabolized as predicted in the clinical trials, it could potentially build up to toxic levels. Different segments of the population metabolize drugs differently, providing a variety of potential reactions to a drug which can impact the dosage, safety, and efficacy of that drug and its usefulness for an individual patient.

A drug and its metabolites may affect other pathways for varying genotypes (or phenotypes). Currently available data on drug safety, as collected by regulators around the world, does not address genetic variances, although hundreds of different reactions are reported to occur in many body systems.

Accordingly, what is needed is an understanding of the impact of differing rates of metabolism on adverse drug events. Additionally, there is a need for a database providing drug safety data as collected by regulators around the world, particularly from a genetic perspective. Further, there is a need for a relational database that can assimilate and correlate these two sets of data, particularly from a genomic perspective.

SUMMARY OF THE INVENTION

Using data, meta-analysis, standardization of terminology and sophisticated association algorithms, the present invention addresses the needs in the above area of drug safety by providing a system of relating drug safety data, adverse reactions, pharmacogenetics, pharmacogenomics and demographic data.

The system described herein is in the area of genomic drug safety, and accordingly provides a method to evaluate existing and/or potential drugs from a genomic point of view. This method takes the drug dimension, with its different characteristics (e.g. chemical class) and adds information regarding the metabolic pathway of drugs (including current and historical drugs), thereby creating genetically relevant taxonomies of drugs. The method also includes demographic information such as the phenotype and genotype of a particular patient involved with a particular reaction (case). These extensions allow the resulting application to correlate drugs with the metabolizing characteristics of specific patient genotypes. As such, the method shows how these drug/genotype interactions lead to increased or decreased chances for particular adverse reactions.

The method creates and utilizes a database which correlates drugs, adverse events and patient characteristics. The method focuses primarily on genetic information, particularly SNPs and gene variants that relate to drugs or drug classes and adverse reactions. Whereas drugs generally metabolize in one or two pathways, adverse events can occur in any of the body systems or pathways, even those not originally believed to be impacted by the drug, leading to extreme complexity.

In accordance with the method, data is collected, for example, from a multitude of sources, and is then analyzed and stored in a standardized data structure. A method of developing "mappings" allows data to be consistently compared and analyzed even if the original sources use incompatible language.

The method takes existing drug data on efficacy and safety, such as is found in drug labels, monographs, and post market information, and solicits new data, such as through clinical trial data in the literature, or from patient and medical histories, and then associates those relationships with patient characteristics including genetic and environmental factors (e.g., diet, age, sex, race, etc.).

The resulting databases can be used in drug research, using the analytic techniques as provided herein can be used to sort among lead compounds to determine those with the lowest possible side effects based on population genetics. It can also be used in prescribing drugs, matching a patient not only to the most efficacious drug, but also to the most effective drug with the least side effects and the lowest required dosage based on the patient's specific genetic and environmental markers.

Since it is possible to check all combinations of genotypes against all drug information, an additional benefit of the present invention is the capability to prepare a database of known relationships and apply them prior to or at the point-of-care (POC). This allows the physician to check a particular patient profile against the drug to be prescribed to assess the risk of an adverse drug reaction for that patient.

The method described herein provides risk analysis of the use of particular drugs based on chemical, proteomic, genomic, and demographic information for both diagnostic and therapeutic purposes. The method uses an innovative complex of tools that associate historical drug safety data with both drug characteristics and patient genetic make-up. One embodiment of the method includes summary data on populations that have had adverse drug reactions along with their genetic profile. Another embodiment provides broad population genetics data for prescribing decisions made on drugs and therapeutics, based on the likelihood of adverse drug reactions. A further embodiment compares individuals with the drug reaction profile of a given population. For example, if a patient profile matches the genetic profile of those prone to liver disorders, then the physicians/pharmacists will avoid prescribing or dispensing drugs with potential adverse liver effects to that patient.

BRIEF DESCRIPTION OF THE DRAWINGS

Certain embodiments of the disclosed invention will now be described in greater detail, and exemplarily shown in the associated drawings in which like reference numerals have been used to indicate like and similar components, arrangements of components, and functional features of the same. The illustrative drawings disclose exemplary and, in some cases, alternative embodiments of the invention, in which regard.

DETAILED DESCRIPTION OF THE INVENTION

The present invention comprises a system and method for creating, storing and using patient-specific and population-based genomic drug safety data including at least one or more integrated databases; a selector for selecting at least one drug for analysis (based on the generic, brand name or therapeutic category); a profiler for displaying statistics that describe one or more behaviors of the drug in multiple dimensions; a series of at least two filters and the means to control the filters individually and in combination; at least one data mining engine. Preferably, the data mining engine is a correlator, a proportional analysis engine, and a comparator; and a graphical user interface for displaying the results of the analysis.

Dimensions such as age, sex, weight, diet, dates, reactions, doses, outcomes, illnesses, report source, and concomitant drugs can be analyzed in combinations of two dimensions, in combinations of three dimensions, in combinations of four dimensions, and other combinations. The method described herein also permits analysis of the association between outcomes and other dimensions.

Figure 1:
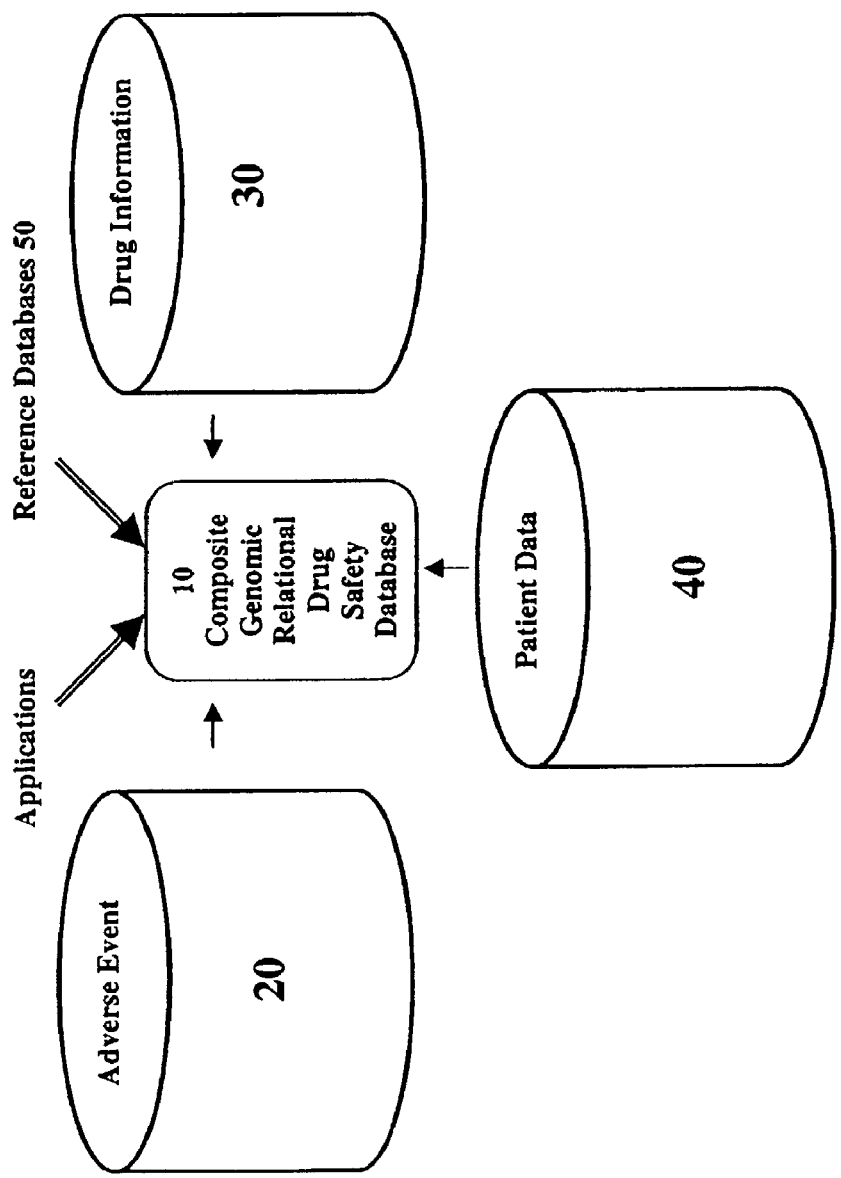
FIG. 1 is a schematic block diagram illustrating one embodiment of a method of mapping various data sources.

FIG. 1 shows the relationship among the various data sources and how data is drawn into a consistent data structure, one that is referenced to standard dictionaries, regardless of which dictionaries were used in the source. In the embodiment of the system and method illustrated in FIG. 1, source data is gathered to create a composite genomic relational drug safety database 10. This source data is collected from databases covering three general areas: adverse event database 20, drug information database 30, and patient or genomic database 40. Adverse event source database 20 includes data on drugs, reactions, demographics and outcomes. Sources of this data are databases such as, but not limited to, the FDA's Spontaneous Regulatory System ("SRS"), the FDA's Adverse Event Reporting System ("AERS"), the World Health Organization Adverse event database, or other country-specific regulatory or epidemiological databases, such as the UK Advert system and the General Practice Research Database (GPRD) as well as other databases and sources, which may be domestic, foreign and/or international in scope. Unexpected or previously unrecognized adverse drug effects can take the form of single reactions, groups of reactions, or increases in a labeled reaction. These adverse reactions may be due to the exposure of a greater number of people to the drug, or the reactions of a particular demographic group. Such information is continually updated as new cases are released and can be added to the information for use in the present method.

Adverse event data 20 may also be provided, for example, from pharmaceutical corporations, hospitals, physicians, health insurers, and state, federal and international agencies. A primary source of pharmaceutical industry data is the individual adverse event databases of the various pharmaceutical corporation safety departments. In each case, source data may be focused on clinical trails, post-market surveillance, research databases, or the like. Unedited data in each source database is referred to as "verbatim." Clinical trial data available in literature includes safety data. Other information is collected and can be accessed from the World Health Organization (WHO), PEM, the General Practice Research Database (GPRD), and so forth.

Drug information source database 30 may include the type or class of drug, metabolic pathways, and drug pharmacokinetics and pharmacodynamics. Such drug source database 30 provides drug taxonomies that offer characteristics of drugs including metabolites, clearance rates, peak serum levels, pharmacodynamics, therapeutic category, chemical structure, or a way to group drugs and explore the relationship to both reactions and genotypes.

Patient source database 40, both records with the name and patent identification removed and summarized records, may include genetic data, demographic, phenotypic, and drug and patient adverse drug reaction ("ADR") history. This source data may be acquired by accessing, soliciting, or assembling data on patients experiencing adverse drug reactions, and comparing the data against data from a control set of a broad population who are not taking the drug/drugs in question in order to see the relationship between certain reactions and genotype/phenotype. For example, light skinned people (a kind of phenotype with genotypic background) are generally prone to sunburn and may additionally be particularly sensitive to certain drugs. Population genetics information includes a wide variety of sources including DNA samples solicited directly from people who have had documented adverse reactions to certain drugs.

In addition to source data, reference data 50 from various accepted canonical references, including dictionaries, thesauruses, taxonomies, and hierarchies, is gathered and used in the genomic drug safety database 10. Examples of such references include the Medical Dictionary for Regulatory activities ("MedDRA™"), National Drug Code Directory ("NDDC"), and the FDA Orange Book. The method described herein has the capacity to substitute and manage both source and reference data.

Figure 2:
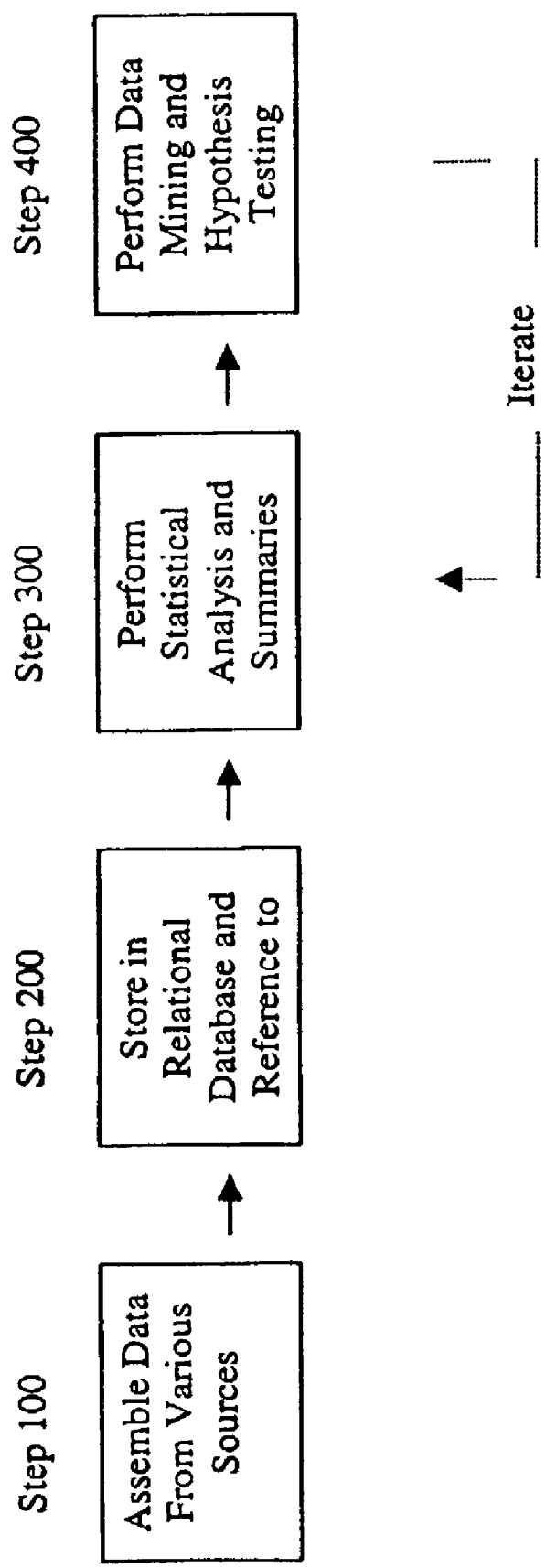
FIG. 2 is a block diagram illustrating one embodiment of the steps utilized in performing the method of the present invention.

The basic steps of the method are shown in FIG. 2. In step 100, data is assembled from sources that relate drugs to reactions and characteristics, and patients to medical history and genotype as described above with respect to FIG. 1. In step 200 of the method, data is implanted into a data structure, information that has been broken down to its most fundamental level is mapped to reference dictionaries, and source data is parsed into a relational database structure. For data sources not already in a relational database structure, transformation from raw source data to a relational structure preferably includes parsing each data source into an image with fields tailored to its corresponding source. Subsequently, the images are consolidated into a single safety table space. Since the database can be simple or complex, the method provides the ability to add many "dimensions" such as age, sex, dates, reactions, doses, outcomes, report source, and concomitant drugs. These dimensions can be entered as structured, narrative, numerical, or categorical variables. Hierarchies in all dimensions (in both preferred and custom paths) are defined as required by the particular end user.

Since several of the most favored data sources are not published in a format that lends itself to direct query, e.g., SRS is available from the U.S. Government only as delimited ASCII data, parsing such data into a relational database model allows the use of leveraging data management tools, which are ineffective on flat files. In preferred embodiments of the present method, the safety table space provides a common set of fields for the parsed source data.

In one method, an information management system integrates data from a plurality of interconnected local databases, providing users with access to a virtual database that ties drug, reaction and patient parameters together. In another method, a record repository is provided for accepting data from a medical service provider and linking it to a patient database, allowing documents for a patient to be retrieved through demographic data. An additional method provides an information extraction system wherein users ask questions about documents in a database and the system responds with information extracted from the documents. In yet another method, copious amounts of data regarding adverse events associated with a particular product are received and analyzed in view of known adverse events associated with the product, providing new uses for the product as well as a catalog of adverse event information for a large number of population sub-groups.

Figure 3:
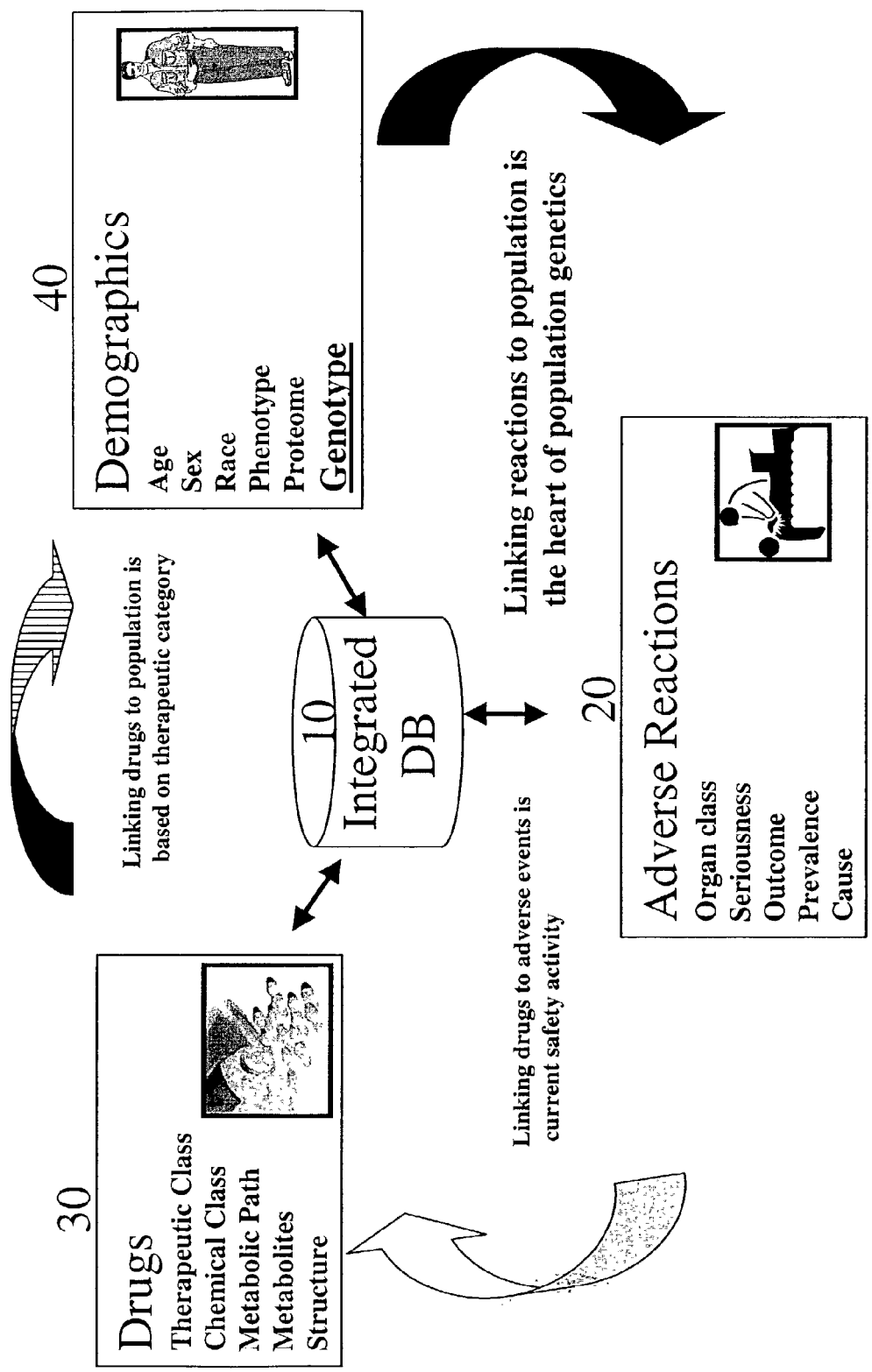
FIG. 3 is a block diagram illustrating one embodiment of the present invention integrating information on drugs, demographics and adverse reactions.

FIG. 3 shows the relationship of three information categories and their various parameters (characteristics). The category entitled "Reactions" of "Adverse Reactions" (20) has been structured by various means: COSTART, WHOART, and most recently MedDRA™. "Reactions" are additionally characterized by their seriousness (e.g. the FDA's "Designated Medical Events," or DME). The method provides a means to integrate these various dictionaries. The second entity is the product or "drug". It is classified by therapeutic class, chemical class, metabolic pathway, metabolites or structure. The method provides a system to integrate these parameters. The last entity, named "demographics," has typically rested on either broad parameters such as age and sex, or on the more specific characteristics of weight, diet, climate, phenotype, proteome, genotype and environment. Recent work in genetics has identified a critical SNP or gene, a defining characteristic for an individual—the genotype.

In one embodiment, data cleanup may be performed independently of parsing source data into a safety database. This allows cleanup to be continual, ongoing, and iterative, either before or after one or more source databases are processed into the pharmacovigilance database which determines if the events are or are not due to the drug. Source database cleanup is an incremental process, proceeding from automated cleanup of certain errors, through human-assisted cleanup of ambiguous entries, to human correction of identified gross errors. Specific cleanup tasks include noise reduction (e.g., suppression of non-alpha characters noise words and combination words), adjustment for misspellings, adjustment for dislocations, transpositions and resolution of possible redundant entries.

In a preferred embodiment, reactions, drugs, and counts of the occurrence (by case and absolute) of each are extracted from the parsed source data. The counts are then grouped. In this embodiment, grouping is by order of magnitude of the count.

In a preferred embodiment, the bulk of data cleanup is performed on a computing platform separate from database storage. A spreadsheet application, such as Microsoft® Excel® is used to track cleanup operations. For example, the first column in such a spreadsheet may contain the verbatim term; the second column may contain a noise-suppressed verbatim term; the fourth column may contain the spell-checked verbatim term, and so on. Other data cleanup applications, such as Metaphone (discussed below), also reside on this separate computing platform. However, cleanup applications need not reside on a separate computing platform, or may be accessible via the Internet or other computer network.

As a part of the data cleanup operation, noise reduction may be performed on the data. Noise reduction involves suppression of words and characters that are typically unnecessary in determining the correct name for drug or reaction verbatim. Noise words and characters include, but are not limited to non-alpha characters (such as numbers, diacriticals, brackets, and control characters), words (e.g., "mg" or "tablet"), combination words (e.g., "20 mg" with no space). For example, both "Tylenol (500 mg)" and "Tylenol Capsules" would be reduced to "Tylenol." A list of noise words and noise punctuation is stored in database tables associated with lexical processing. Non-alpha characters, such as control characters, are also suppressed at this stage.

After noise reduction, misspellings are detected and corrected using known tools such as spell checkers, sound-alike suggestion programs, a verbatim replacement table, and human inspection. A preferred spell checker operates on noise-suppressed verbatim terms, making a series of spelling variations on terms not found in the reference sources. These variations are used as the basis for searching reference sources and suggesting candidate canonical terms. Reference sources include standard and special-purpose dictionaries. The variations introduced include:

- adding an extra character to the term, e.g., allowing noise-suppressed verbatim such as "proza" to be searched as "prozac";
- removing a character from the term, e.g., allowing noise-suppressed verbatim such as "prozzac" to be searched as "prozac";
- swapping adjacent characters, e.g., allowing noise-suppressed verbatim such as "rpozac" to be searched as "prozac."

In addition to a spelling suggester, a sound-alike program, such as Metaphone or Soundex is employed to suggest variations. Metaphone is a published phonetic code algorithm similar to Soundex, which is a sound based indexing system. Every word has a four-letter Metaphone value that can be calculated. The Metaphone suggester calculates the Metaphone value for each entry in the reference sources and for each unresolved verbatim term. Those reference source terms having a Metaphone value matching that of an unresolved verbatim term will be offered as a suggestion to a database developer for resolution. For example, the Metaphone value for both "prosac" and "prozack" is PRSK; the Metaphone value for both "Claritin" and "Klariton" is "KLRT." Where no candidates satisfy the developer, an option is provided for accepting a surrogate term from the developer.

Various embodiments of the method described herein include steps for capturing and using domain specific lexical knowledge not easily applied through noise reduction or spell checking. At the basic level, this amounts to use of a replacement table, containing mappings from known errors to corrected canonical terms. On a more sophisticated level, as domain-specific knowledge is accumulated, autocoders are employed to capture human decision-making experience regarding cleanup.

Human interaction is particularly useful in identification and correction of dislocation errors, i.e., where a term valid in one field (e.g., headache/reaction) appears in a field where it is not valid (e.g., headache/drug). Dislocation errors are identified in preferred embodiments where a term does not fit the type of the field it is found in, but nonetheless exists in reference sources outside the scope of the particular field.

Redundant entries are identified and removed with operator assistance. A "case" may include all data regarding the adverse events experienced by one person taking a drug. A sequence of events regarding a single individual taking a drug should not be recorded as separate cases (potentially duplicating the adverse events associated with the case). This is important for correct statistical views of the data. The method provides tools to operators to allow identification and consolidation of redundant cases. In preferred embodiments of the present invention, multiple cases involving the same person over a contiguous period are presented to an operator for determination as to whether or not such entries actually represent one case with multiple (or possibly single-occurrence, multiple-reported) events.

For example, if a case concerning an "eye pain" reaction is amended fifteen times, only one instance of eye pain should be aggregated for this individual case. Through record linking, preferred embodiments of the method match successor reports with their predecessors using data inherent in the records, and compare other information in the records to gauge the quality of the match. For example, two cases may match on the "case identification" field, or a "drug manufacturer identification" field, or a "report date." Those cases known to be redundant, and those cases showing a link between records, are presented to researchers for resolution. In alternate embodiments, resolution between likely redundant cases is accomplished via an expert system.

It should be understood that underlying verbatim terms are not changed by application of noise suppression, the use of spell checkers, the resolution of dislocations, or the resolution of redundant entries. Verbatim terms, such as drug and reaction terms, that have been parsed into a safety database and cleaned are then mapped to "tokens" from the reference data sources. The word "token" refers to the specific term(s), from one or more of the reference sources, that is associated with one or more of the verbatim terms in a manner that allows a search for the token to return results containing the verbatim term(s) linked to the token. Where an exact match exists between a verbatim term (source or cleaned) and a reference term, the verbatim term is mapped to the reference term as token. Where no exact match is found between verbatim (cleaned or otherwise) and reference data terms, the present invention presents a series of steps for resolving such unmatched terms.

In addition to corruption in verbatim data, valid variations in terminology may also be resolved through mapping to reference data tokens. For example, "PROZAC" and other trade names for flouxetine are preferably mapped to the generic "flouxetine." In another example, luliberin, gonadotropin releasing hormone, GnRH, gonadotropin releasing factor, luteinizing hormone releasing hormone, LHRH, and LH-FSH RH are equivalents and may be considered as such for analyzing adverse effects. Furthermore, different chemical derivatives, such as esters, salts, or acidic or basic forms of the same drug may be grouped together, where a reference data term exists, under the same token in order to analyze adverse drug events.

In accordance with the method, source data verbatim terms may be nominated as token candidates; frequency of occurrence and absolute count being typical bases for nominating a term as a token candidate. Verbatim drug, patient and reaction terms may be grouped by order of magnitude of absolute count. For reactions, token candidates are chosen from accepted reference sources such as MedDRA™, Coding Symbols for a Thesaurus of Adverse Reaction Terms ("COSTART"), GPRD, and World Health Organization Adverse Drug Reaction Terminology ("WHOART"). For drugs, token candidates are chosen from corresponding canonical sources such as the National Drug Code Directory ("NDCD"), WHO Drug Dictionaries for drugs, and the FDA's Orange Book.

Individual verbatim terms are then mapped to the selected tokens. According to the present method, this process may be used for multiple database dimensions in addition to drug and reaction, e.g., outcomes, where the definition of "serious" outcomes can differ over time and between reference sources.

This mapping enables those searches of the database focused on tokenized fields, e.g., drug, patient, and reaction fields, to be executed with greater confidence. Using the mapping approach, variability in source event data entry, typically a difficult-to-control aspect of data collection on a large scale, is mitigated as a source of error.

Corrected verbatim is mapped to reference canonical terms and structures. As noted earlier, where an exact match exists between a verbatim term (source or cleaned) and a reference term, the verbatim term is mapped to the reference term as token. Where no exact match is found between verbatim (cleaned or otherwise) and reference data terms, the method presents a series of steps for resolving such unmatched terms. In those instances where a user is presented with a number of assigned unresolved entries, the method presents the user with suggestions identified by lexical processing (e.g., Metaphone, fixed list) for each unresolved verbatim term. The user may then select from this list or enter a surrogate term. After selecting a candidate term or entering a surrogate term, a list of generic drug names will be shown (if the matched term was indeed a trade name rather than a generic). At this point, a user can either save the mapping or modify the list of generic terms. This last option will allow a user to override the list of generics or to enter new chemical compounds as they are developed.

Cleaned source data reaction terms may be mapped to standardized hierarchies such as WHOART, COSTART, and MedDRA. Specifically, cleaned source data reaction terms are mapped to multiple levels (and possibly multiple entries within a level) of the hierarchy. In preferred embodiments, mapping of cleaned verbatim reaction terms proceeds in a fashion similar to mapping of drug terms. While the preferred embodiments perform mapping on cleaned source data, it should be understood that mapping may be performed on uncleaned, or even unparsed, source data.

Transparency in the process of moving from source data verbatim terms to a cleaned safety database with verbatim terms mapped to tokens is important to both database developers/operators and to end users. The present method captures the way source data terms have been cleaned and mapped as the "pedigree" of each term. The pedigree of a term is the link between the mapped term and the decisions made during data cleanup. End users typically wish to verify the pedigree of the data they use. In those embodiments, retained data includes one or more of the following as appropriate: verbatim term, token mapped to, source of the verbatim term, number of occurrences of the verbatim term, number of cases in which the verbatim term appears, which type of cleanup (if any) was performed, a cross-reference to where the token is defined, and dates of the earliest and latest reported occurrence.

The method may be implemented on a single computer or across a network of computers, e.g., a local area network or on or across the Internet. Preferred embodiments include implementations on computer-readable media storing a computer program product performing one or more of the steps described herein. Such a computer program product contains modules implementing the steps as inter-related functions as described herein. In a networked implementation, the databases, data management software and analytical software may reside in any combination of one or more local workstations and one or more network servers.

As described above, the database used in the present method sets up different information sources in a composite relational data structure, as illustrated in FIG. 3. This composition correlates patient information 40 (demographics, genetic make-up, environment), drug information 30 (class, therapeutic use, structure), and events of adverse reactions 20 (at different levels of detail). Along with DNA sample references and detailed individual medical histories, these are assembled and referenced into cases. The information in these cases includes both the verbatim data from the original sources as well as a standard reference dictionary term for each element of data. The latter is critical to ensure the ability to compare cases across drugs, patients and events.

Referring again to FIG. 2, in step 300 of the method, described herein, statistical associations are analyzed. The present method looks at cases and determines two outcomes:
 a. Whether there is an indication of association among a drug, a reaction or group of reactions, and a genotype
 b. The distribution of that association in a population.

The first outcome is determined from one of four techniques
 1. Proportional analysis against a variety of backgrounds,
 2. A correlation of two or more parameters (e.g., Pearson product-moment correlation coefficient),
 3. Differential analysis (i.e., changes over time or another dimension), and
 4. Neural networks (one of several paradigms that associate items and provide weights based on the statistical distribution of outcomes), or other machine learning algorithms such as Hidden Markov models, Bayesian networks and kernel methods among other methods known in the art.

Note that the method provides a way to apply these techniques, in a novel way, to categorical variables. That is, variables that retain non-numeric values. Reactions such as headache, rash, genotype, drug chemical class, etc. are the key parameters. The application of the Pearson Product-Moment using a binary scale (0 or 1) that means that one of possibly hundreds of parameters is there or not there, is a unique application of the Pearson technique. This application of the Pearson P-M rests on the ability of the method to link data to consistent dictionaries and also calculates millions of pairs.

Various methods are available according to the present method for using the database to analyze relationships. The database provides a classification taxonomy structure for drug and genomic data. As taxonomies develop over time (typically based on new ways of grouping drugs or new ways of grouping SNPs and gene variants), the method provides parameters and hierarchies to enable richer correlations. As drugs or genes are grouped, they provide the basis for "coherent processing" in signal detection, i.e., they have the ability to group information to reinforce the "signal" that a particular drug or genotype is, in fact, a possible cause of a reaction. Similar structures are used for reactions and outcomes (e.g., hospitalization or death) as well as a drug classification template that allows mapping between drug and pathway, proteome, drug classification and others, in search of potential associations at the drug level; and a SNPs and gene classification template that allows a variety of high/medium/low level detail (e.g., broad SNPs region for certain reactions to specify SNPs related to Stevens-Johnson Syndrome).

The present method analyzes the multivariate relationships of drug safety, therefore making the database more usable to researchers and clinicians. Many aspects of the use of drug, reaction, and genetic/environmental information depend on having the ability to consolidate data across many different databases, with specific applications of standard categories and standard dictionaries allowing the consolidated data to provide meaning. These applications include: a database on demographics, drugs, reactions, and outcomes linked to standard dictionaries; a selector/profiler/filter that allows a researcher to hypothesize on (i.e., groups of reactions or symptoms) and filter confounding elements (e.g., the known pathway effects etc.) in order to enhance the ability to uncover unwanted effects, by analyzing similar drugs chemically, or pathways genetically; a set of analytical engines that respectively analyze different aspects of the database (which is basically organized into historical or current "cases", i.e. a patient), with a certain drug or drugs, and with certain reactions and outcomes. These include: proportional Engines (PRR, OR) that look for anomalies against a background; correlators that look for associations; differing engines that compare different sets of data (e.g., one population or another) in search of variations; Neural Network and other learning machine paradigms that apply heuristics to large databases in order to model and classify, e.g. by comparing weights of associations; a set of data display, viewing and visualization that helps the researcher use his/her insight and pattern recognition capabilities to see, for example, genetic patterns or patterns of pathways that are involved for certain genotypes. The present method then, uses both automated and semi-automated techniques to blend and create the best data mining and hypothesis testing.

Even though the efficacy of a given drug may only involve one or two metabolic pathways, and therefore body systems, adverse reactions may stem from one or several of the many different pathways inherent in the human organism. Thus, the present method combines detection as well as association algorithms to help identify the relationships among a drug, a given patient genotype, and the reactions and outcomes that could result.

Based upon the above, the present method accesses the system database, wherein a set of cases may be selected for analysis. Having selected the case-set of interest, the method then preferably proceeds to a profile, which preferably displays statistically-derived values that describe the behavior of the drug of interest based upon patient genotype. From the profile, the method can then preferably proceed to employ one or more filters that permit recalculation of the statistics by selecting among available variables. Once a set of cases is determined, for example, by the use of one or more filters, the cases can then preferably be submitted to one or more data mining engines. Such data mining engines may include a correlator engine, which provides information on analyses that have been previously completed—including date and time, task number, and generic drug. Each listing ends with a hyperlink that a user can employ to view the results of a search. A "delete" function is preferably provided to manage this list.

Step 400 of the method provides the data mining and extraction capabilities in which the results of statistical analysis in step 300 are compared against selected thresholds or criteria to extract the data of interest. Based on the above techniques, each dimension in the present invention will have a natural "filter" framework based on the number of parameter (dimension) variables and their number in the database. Within this framework, one or more of a combination of filters can be used to select "cases" and perform a restricted analysis of step 300. This interaction between steps 300 and 400 allows an individual researcher to use his/her hypothesis to adjust the analysis. For example, a set of adverse events are really a reflection of non-efficacy of a certain drug, such as reported adverse event of "depression" for a patient taking an anti-depressant. These reactions could be filtered out as part of step 300.

Output from the data mining engines is preferably displayed using a graphical viewer, which permits the user to present the data in a variety of formats, including, but not limited to a sortable table, a sortable line listing, and a radar screen, thus, allowing rapid identification of signals and providing the user the ability to drill down to individual case details.

Alternatively, in another preferred embodiment, the method of the present invention permits choosing a profile, applying one or more filters, processing the set of cases using the data mining engines, and displaying the results for a user or viewer.

The present invention therefore includes a means to assemble data, create a database, and finally produce a summary and individual outputs based on the implied parameter "triplet" consisting of patient, drug, and adverse event data. The result is a structural database that combines a variety of drug characteristics, drug class and pathway characteristics, and population as well as individual genetics. The present invention provides a method for applying genomic-based adverse event data in a drug lifecycle. There are many research and medical situations where it is critical to associate individual patient's genotype or the general population's genetic distribution to Adverse Drug Reactions ("ADRs"). The ADR arena is complex because it involves many possible human metabolic pathways. Due to this complexity, and the extremely difficult tracing of hundreds or thousands of possible causes for thousands of reactions, the database of the present invention was developed based on clinical outcomes. In this respect, the system and method works backward from ADRs toward the statistical distribution of genotypes potentially associated with the event. The grouping of SNPs and gene variants provides a "cluster" that can be associated with a higher-than-expected reaction. For example, it may be that roughly 1% of patients experience headache with a particular drug, but 30% of those patients sharing a particular genotype have experienced headache with the drug. This may potentially link that genotype to headaches associated with the drug.

With efficient and effective analysis of adverse drug effects, pharmaceutical research and development professionals can learn more details of the reaction profiles of drugs and the at-risk populations who may be prescribed those drugs. This information would allow a more effective selection of lead compounds and would ultimately lead to development of drugs with reduced risk of adverse effects.

The system and method disclosed herein may be used during the research and pre-clinical trial stage of drug development for reviewing a set of drugs against the genetic background of a population in order to determine the ADR profile. The system and method may also be used during clinical trials, comparing the actual experience of ADRs with the database, for example, using proportional analysis (or any of the above techniques) to see if the trial population exhibits unexpected adverse events. The system and method may additionally be used during the diagnosis and prescription process at a point of care for checking a particular patient's genetic profile against a drug to assess or determine the probability of an adverse drug reaction for a drug (especially those considered serious by the healthcare provider) compared to other drugs. The system and method may further be used on a continuing basis for collecting post-market data on drugs by retrieving the genetic profile of patients exhibiting adverse events for a drug, and updating the present invention database with this information.

It should be appreciated that in all these genetic comparisons, there is potential to identify phenotypic markers (e.g. blue eyes, blond hair, fair skin—people of Nordic decent) with genotypes. In addition, environmental factors such as diet, work, or smoking habit may be related as well.

The system and method further utilize a drug utilization review ("DUR"), incorporating the genomic dimension to the patient specific DUR. DUR application uses the link among the three elements discussed above, drug reactions and genotype, to create methods for avoiding ADRs for a given patient. With the knowledge of the genomic drug safety database, there is an established association of certain SNPs and gene variants of an individual that are associated with a drug and its reactions. By having background tested, or through an understanding of a person's genotype or phenotype from clinical evidence (for example, a person who does not metabolize and respond to fluoxetine can be presumed to poorly metabolize CYP (2D6) related drugs. If the database shows certain ADRs with such a person, the DUR application of the database would assess the drug and rate its potential for adverse reactions for that individual. Other factors, such as environment, nutrition, foodstuffs, beverages, exposure to toxins, chemicals, supplements, herbal remedies, and the use of other drugs, would also continue to be considered, based on the best available evidence.

To formulate risk of drug safety, the system and method assign a risk parameter that combines drug, genetic, and outcome information of drugs on the drug label, to create a rapid means to improve drugs for an individual patient, or assess the risk of a specific drug for that patient.

The system may assign a PIN to an individual, and then provide a means by which to query the database on the relative risk for a drug, as described below. By using a PIN based system, there is provided the maintenance of privacy.

The method and system described herein may be embodied in a network environment. Such an implementation enables the DUR application in a web-based system, where a central (or other network accessible means) is used to allow access to the check of drugs from any location. A subscriber would be provided the information in the background. Others would enter the PIN and drug and the resulting assessment of the risk would be returned. As a means for universal understanding of the results, a scale could be used (such as described below). This method would allow any subscriber or enrollee to a healthcare program using the method to input genomic data from any location, for example, a genomics lab that examines the patient, or enrollees profile. The data on other aspects of the patient would similarly be entered, all via PIN. Then, at any time, the DUR application would allow network access to the risk assessment.

The present method may use a parameter or coefficient specifically designed to measure risk. Although many weightings may be used, this parameter would provide, on a suitable scale (e.g., 0 to 1.0 or other normalized scale), a weighted assessment of genetic risk for the patient based on the probability that certain drug reactions are likely for the patient genotype. The scale takes into account the closeness of the drug to the drug in the database (it could only share chemical class) and the closeness of the genetic profile of the patient to the average genetic profile of the database, again using a closeness fraction based on the number of standard deviations from the mean fit. This scale would then provide a nominal risk, with an error range, for the individual. Any actual scale that uses a linear, or logarithmic weighting (or other), that accounts for a closeness adjustment for the drug and for the genotype, will then be used to report the expected ADRs. Note, in the preferred embodiment, the most serious reaction would be used and weighted more heavily (using, for example, the FDA CDER Designated Medical Event list).

The scale would be refined over time as better tests and more population statistics are added. Thus, both the database and the precision of the scale will improve over time. The use of a numerical range that healthcare providers become accustomed to will allow ease of interpretation of the results.

The method described herein provides for personalized medicine application in drug safety. The system and method draw a relationship between genetic type and predispositions to adverse reactions for certain drugs or drug types. Given a sufficient set of specific genetic information on an individual, there exists the potential to create a "profile" for that individual.

Unlike the relationship of genetic information to diseases, where only a few genes, or SNPs may be involved, the realm of adverse events involves numerous other areas of an individual's metabolism. In fact, it goes beyond that to include the influence of environmental factors such as coffee drinker, smoker, traveler, etc., that changes an individual's environment and medical situation into which drugs are prescribed. The system and method allow, for example, an individual's profile to be privately stored and accessed via a PIN. Then, given the drug a physician is considering, the patient's background can be checked for potential risk.

As disclosed herein above, various embodiments of the system and method provide several benefits. These benefits include warning a patient or physician that certain drugs have produced reactions associated with the patient's genotype; a broad understanding of gene and SNP relationships to pathways, proteome and drugs in those pathways; a statistical understanding of the genetic behavior of drug classes; a structural database that allows a drill-down on genetic differences for more specific reactions; a database that makes ADR profile associations with proteome possible; a database that increases the potential to uncover the multiple ways certain ADRs could develop; a method for scoring the genomic based risk of certain adverse events for drugs or drug classes; a method for preserving patient privacy while permitting clinical labs, physicians, etc., to access the information for a particular patient; adjustment of the genetic risk by correlation with environmental factors; a method for adding details to the genomic database as new information is made available; a broad, statistical understanding of population genetic impact on the percentage risk of certain adverse events with certain drugs or drug classes; and a method for adding data from sources that may have been based on different vocabularies.

Although the present invention has been described and illustrated in detail, it is to be clearly understood that the same is by way of illustration and example only, and is not to be taken as a limitation. The spirit and scope of the present invention are to be limited only by the terms of any claims presented hereinafter.

What is claimed is:

1. A method for assessing and analyzing one or more drugs, adverse effects and associated risks, and patient information resulting from the use of at least one drug of interest, comprising:

collecting data from a plurality of sources comprising drug information, adverse effects relating to drugs and patient information;

placing collected data into a data structure, wherein data from sources not already in a relational database structure are parsed into a relational database structure;

generating a relational database for relating drug information, adverse effects and patient information;

assembling said patient information, drug information and adverse effects into individual cases, wherein each said case contains patient information, information related to a drug administered to that patient and a description of an adverse drug reaction;

identifying a patient genotype and at least one drug proposed to be administered to a patient having said genotype;

using said relational database to conduct statistical analysis across a set of cases to determine whether there is an indication of association among a drug, a reaction or group of reactions and a genotype and the distribution of that association in a population;

creating a profile comprising the results of said statistical analysis that describes the behavior of the drug of interest based on patient genotype from multiple cases related to the safety of the at least one drug, wherein one or more filters is employed to select among available variables to permit recalculation of the statistical analysis;

submitting the results of the statistical analysis to at least one data mining engine to compare said results against selected criteria to extract data of interest; and displaying the output from the data mining engine through an output device;

wherein the analysis of the data collected involves parsing a population segment data into a plurality of population segments, the population segments having differing rates of metabolism;

wherein the analysis of the data collected involves parsing a drug safety data based on a genetic perspective;

wherein the drug of interest is analyzed using two or more metabolic pathways;

wherein a first metabolic pathway includes the parsed population segment data relating to population segments having differing rates of metabolism;

wherein a second metabolic pathway includes the parsed drug safety data relating to drug safety data based on a genomic perspective;

wherein the first and the second metabolic pathways are assimilated; and wherein the first and the second metabolic pathways are correlated.

2. The method of claim 1, wherein analyzing using a data mining engine comprises correlating or proportionally comparing any two data types, wherein the data types are drug, adverse effects, or patient demographics.

3. The method of claim 1, wherein the data is cleaned, wherein cleaning comprises removal of noise, spell checking, and removal of redundant entries.

4. The method of claim 1, wherein the relational database comprises stored data which is mapped to tokens, wherein a token comprises a standardized search term.

5. The method of claim 4, wherein a token is selected from the group of reference sources consisting of MEDRA, WHO Drug Directories, FDA Orange Book, COSTART, NDCD, GPRD, and WHOART.

6. The method of claim 1, wherein the steps are performed in a network environment.

7. The method of claim 1, wherein the patient information comprises age, sex, weight, diet, reactions, environment, illness, dosage, genotype, outcome, report sources, or concomitant drugs.

8. The method of claim 1, wherein the data mining engine comprises a correlator, a proportional analysis engine, or a comparator.

9. The method of claim 1, further comprising:
predicting when the drug of interest fails to metabolize at a predetermined rate;
predicting when the drug reaches a predetermined toxic level in the patient; and
displaying a plurality of potential adverse drug reactions the patient may exhibit based on the analysis and the correlation of the metabolic pathways,
wherein the predetermined rate is determined in a clinical drug trial.

10. The method of claim 9, further comprising:
changing a variable;
determining whether the variable change affects the patient's safety;
determining whether the variable change affects an efficacy of the drug; and
displaying one or more results of the variable change,
wherein the variable change comprises changing a drug dosage for the drug of interest.

11. The method of claim 1, further comprising:
correlating the patient information, the drug information, and the events of adverse reactions information;
displaying the resulting correlation,
wherein the patient information being correlated and displayed comprises demographics, genetic make-up, and environmental factors, said environmental factors comprising a diet information, an exercise information, a smoking habits information; a travel information, and a coffee drinking information;
wherein the drug information being correlated and displayed comprises the class of the drug, the therapeutic use of the drug, and the structure of the drug; and
wherein the events of adverse reactions being correlated and displayed comprise differing levels of detail concerning the events.

12. The method of claim 1, further comprising combining a detection algorithm and an association algorithm, wherein the combination assists a user in identifying a relationship between the drug of interest and a second drug, the patient genotype, and the adverse drug reaction.

13. The method of claim 1, further comprising displaying one or more statistically derived values, wherein the values displayed are correlated with the drug of interest based on the patient genotype.

14. The method of claim 1, wherein the displaying further comprises a viewing-and-visualization of the drug of interest based on the patient genotype.

15. The method of claim 14, wherein the viewing-and-visualization of the drug of interest includes assisting a user of the method in a pattern recognition capability, the pattern recognized being a genetic pattern or a pattern derived from the analysis and the correlation of the first metabolic pathway and the second metabolic pathway.

16. The method of claim 14, wherein the viewing-and-visualization includes a pattern recognition capability, wherein the pattern recognized being comprising a genetic pattern a pattern of the first metabolic pathway, a pattern of the second metabolic pathway, or a combination of the first and second metabolic pathways.

17. The method of claim 14, wherein the viewing-and-visualization further comprises a mapping of a one or more terms, the mapping comprising linking a term related to the drug or an adverse effect term to a token, the token being a term located in the reference source;
wherein, in a first state, when a match exists between the drug or the adverse effect term and the token, the drug or the adverse effect term are mapped;
wherein, in a second state, when no match exists between the drug or the adverse effect term and the token, the unmatched term is labeled as an unresolved term; and
wherein a vocabulary processing identifies a suggested word for the unresolved term.

18. The method of claim 17, further comprising:
using the vocabulary processing to determine a candidate term, the candidate term being related to a drug or an adverse drug reaction;
selecting the candidate term; and
saving the mapping or modifying a list of the one or more suggested words identified by the vocabulary processing.

19. The method of claim 17, further comprising:
entering a surrogate term; and
saving the mapping or modifying a list of the one or more suggested words identified by the vocabulary processing.

20. The method of claim 17, wherein the mapping further comprises verifying the term,
wherein the verification involves forming a visual map,
wherein the visual map comprises the term, the number of cases in which the term appears, a cross-reference to where the token is defined in the original source, a calendar date of the earliest reported occurrence of the term, and a calendar date of the latest reported occurrence of the term.

21. The method of claim 1, the assembling step further comprising:
correlating a one or more DNA sample references and the one or more detailed individual medical histories;
wherein the case comprises both a verbatim data from one or more original sources and a standard reference dictionary term for each element of the data; and
wherein the case is configured for comparing cases across drugs, patients, and events.

22. The method of claim 1, the analysis from a genomic perspective further comprising:
checking a genetic profile of the patient against a drug to assess or determine the probability of an adverse drug reaction for the drug of interest compared to one or more other drugs,
wherein the checking further comprises:
matching a characteristic of the drug of interest with the metabolic pathway of the one or more other drugs;
creating a plurality of taxonomies of the drugs, the plurality of taxonomies describing one or more characteristics of the drugs;
displaying the genetically relevant taxonomies of the drugs;
wherein the taxonomies comprise metabolites, clearance rates, peak serum levels, pharmacodynamics, therapeutic category, chemical structure;
wherein the displaying of the taxonomies comprises a way of grouping drugs and determining the relationships of the adverse drug reactions and the genotypes;
wherein the relationship comprises the phenotype and the genotype of the patient and the case; and
wherein the case comprises the adverse reaction to the drug.

23. The method of claim 1, further comprising:
collecting post-market data on the drug of interest by retrieving the genetic profile of a plurality of the individuals exhibiting adverse events for a drug; and
updating the relational database with the retrieved genetic profile.

24. The method of claim 22 further comprising:
displaying a result of correlating the drugs with the metabolizing characteristics of the patient genotypes;
predicting, in a first state, how the drug interactions or the genotype interactions increase a likelihood for one or more adverse reactions; and predicting, in a second state, how the drug interactions or the genotype interactions or decrease a likelihood for one or more adverse reactions.

25. The method of claim 1, wherein the analysis further comprises:
finding an association among a drug, a reaction, or a group of adverse drug reactions, and a genotype; and
finding a distribution of the association in a patient population,
wherein the technique for finding the association among a drug, a reaction, or a group of reactions, and a genotype comprises any of a proportional analysis against a variety of backgrounds, a correlation of a plurality of parameters, a differential analysis, a use of neural networks, or a use of learning algorithms comprising Hidden Markov models, Bayesian networks, and kernel methods.

26. The method of claim 25, wherein a parameter, used to find the association among a drug, a reaction, or a group of adverse drug reactions, retains its non-numeric value;
wherein the parameter is a mathematical expression that correlates an adverse drug reaction, a genotype, or a drug chemical class;
wherein determining the association among the drug, the reaction, or the group of adverse drug reactions comprises applying the mathematical expression;
wherein a result of applying the mathematical expression involves a binary scale, the scale having a "0" that corresponds to having no association and a "1" that corresponds to having the association;
wherein determining the association further comprises linking data to a consistent dictionary; and
wherein the mathematical expression comprises the Pearson Product-Moment.

27. A system for assessing and analyzing one or more drugs, adverse effects and associated risks, and patient information resulting from the use of at least one drug of interest, comprising:
a relational database comprising source data, wherein the source data comprises adverse event data, drug information and patient information, wherein data form sources not already in a relational database structure are parsed into a relational database structure;
an assemblage of cases comprising patient information, drug information and adverse effects, wherein each said case contains patient information, information related to a drug administered to that patient, and a description of an adverse drug reaction;
a selector for selecting one or more cases for analysis;
a profiler using statistical analysis conducted by said relational database across a set of cases to determine whether there is an indication of an association among a drug, a reaction or group of reactions and a genotype and the distribution of that association in a population, wherein profiles created by said profiler comprise the results of said statistical analysis that describes the behavior of the drug of interest based on patient genotype from multiple cases related to the safety of the at least one drug, wherein one or more filters may be used to select among available variables to permit a recalculation of the statistical analysis;
at least one data mining engine for submitting the results of the statistical analysis in order to compare said results against selected criteria to extract data of interest; and an output device for displaying the output from the data mining engine;

wherein the analysis of the data collected involves parsing a population segment data into a plurality of population segments;

wherein the analysis of the data collected involves parsing a drug safety data based on a genetic perspective;

wherein the drug of interest is analyzed using a plurality of metabolic pathways;

wherein a first metabolic pathway includes the parsed population segment data relating to population segments having differing rates of metabolism;

wherein a second metabolic pathway includes the parsed drug safety data relating to drug safety data based on a genetic perspective;

wherein the first and the second metabolic pathways are assimilated; and wherein the first and the second metabolic pathways are correlated.

28. The system of claim 27, wherein analyzing using a data mining engine comprises correlating or proportionally comparing any two data types, wherein the data types comprise drugs, adverse effects, or patient.

29. The system of claim 27, wherein the data is cleaned, wherein the cleaning comprises removal of noise, spell checking, and removal of redundant entries.

30. The system of claim 27, wherein the relational database comprises stored data which is mapped to tokens, wherein a token comprises a standardized search term.

31. The system of claim 30, wherein a token is selected from the group of reference sources consisting of MEDRA, WHO Drug Directories, FDA Orange Book, COSTART, NDCD, GPRD, and WHOART.

32. The system of claim 27, wherein the system is configured to operate in a network environment.

33. The system of claim 27, wherein the patient information comprises age, sex, weight, diet, reactions, environment, illness, dosage, genotype, outcome, report source, or concomitant drugs.

34. The system of claim 27, wherein the data mining engine comprises a correlator, a proportional analysis engine, or a comparator.

35. A method for assessing and analyzing one or more drugs, adverse effects and associated risks, and patient information resulting from the use of at least one drug of interest, comprising:

collecting data from a plurality of sources comprising drug information, adverse effects relating to drugs and patient information;

cleaning the collected data;

placing the collected data into a data structure, wherein data from sources not already in a relational database structure are parsed into a relational database structure;

generating a relational database for relating drug information, adverse effects and patient information;

assembling said patient information, drug information and adverse effects into individual cases, wherein each said case contains patient information, information related to a drug administered to that patient and a description of an adverse drug reaction;

identifying a patient genotype and at least one drug proposed to be administered to a patient having said genotype;

using said relational database to conduct statistical analysis across a set of cases to determine whether there is an indication of association among a drug, a reaction or group of reactions and a genotype and the distribution of that association in a population;

creating a profile comprising the results of said statistical analysis that describes the behavior of the drug of interest based on patient genotype from multiple cases related to the safety of the at least one drug, wherein one or more filters is employed to select among available variables to permit recalculation of the statistical analysis;

submitting the results of the statistical analysis to at least one data mining engine to compare said results against selected criteria to extract data of interest; and displaying the output from the data mining engine through an output device;

wherein the cleaning of the collected data includes identifying a synonymous term, a misspelling of a term, or a variation of a term for the drug or a term for the adverse effect;

wherein the cleaning of the collected data further includes labeling the identified term as a verbatim term;

wherein the analysis of the collected data involves parsing a population segment data into a plurality of population segments, the population segments having differing rates of metabolism;

wherein the analysis of the data collected involves parsing a drug safety data based on a genetic perspective;

wherein the drug of interest is analyzed using two or more metabolic pathways;

wherein a first metabolic pathway includes the parsed population segment data relating to population segments having differing rates of metabolism;

wherein a second metabolic pathway includes the parsed drug safety data relating to drug safety data based on a genomic perspective;

wherein the first and the second metabolic pathways are assimilated; and wherein the first and the second metabolic pathways are correlated.

36. The method of claim 35, further comprising:

maintaining a transparency between the data source terms and the cleaned data terms, the transparency comprising:

mapping the verbatim term in the relational database to a token in the data source reference, visually displaying a link between the source reference term and the cleaned relational database term, wherein the display comprises a verbatim term, a token mapped to the verbatim term, a source of the verbatim term, a number of occurrences of the verbatim term, a number of cases in which the verbatim term appears, a type of cleanup performed, a cross-reference to a source data reference in which the token is defined, a calendar date of the earliest reported occurrence, and a calendar date of the latest reported occurrence.

37. The method of claim 35, further comprising:

reducing a background noise in the parsed data, detecting misspellings of a drug or an adverse effect reaction;

correcting the misspellings detected;

operating a spell checker, a spelling suggester, a sound-alike spelling suggestion program, or a verbatim replacement table;

making a series of spelling variations on terms not found in the reference sources;

searching the reference sources;
suggesting a candidate canonical term,
   wherein the background noise reduction suppresses words and characters that are unnecessary for determining the name for a drug term or a adverse effect reaction term
wherein the reference sources include standard dictionaries and special-purpose dictionaries.

38. The method of claim 35, wherein a sound-alike spelling suggestion program is Metaphone or Soundex,
   wherein the suggester calculates the Metaphone value for each entry in the references sources and for an unresolved verbatim term, the unresolved verbatim term being a term that could not be matched with a reference source.

39. The method of claim 35 further comprising:
   assessing the genetic risk for the patient based on the probability that certain drug reactions will occur for the patient genotype,
   weighting the genetic risk on a scale, the scale accounting for a closeness of the drug to a drug in the relational database and the closeness of the genetic profile of the patient to the average genetic profile of the database; and
   reporting the expected adverse drug reaction.

40. The method of claim 39 further comprising weighting the most serious adverse drug reaction more heavily on the scale.

* * * * *